United States Patent [19]
Shetty

[11] Patent Number: 5,882,641
[45] Date of Patent: Mar. 16, 1999

[54] FRUIT POMACE COMPOSITIONS AND USES THEREOF

[75] Inventor: Kalidas Shetty, Amherst, Mass.

[73] Assignee: University of Massachusetts, Boston, Mass.

[21] Appl. No.: 771,048

[22] Filed: Dec. 20, 1996

[51] Int. Cl.[6] ........................................ C12N 1/14
[52] U.S. Cl. .............................................. 424/93.5
[58] Field of Search ............................... 424/93.5

[56] References Cited

U.S. PATENT DOCUMENTS 5,232,850  8/1993  Casida, Jr. ........................... 435/253.3

OTHER PUBLICATIONS

Lewis et al., Biocontrol Science and Technology 6(2):163–173 (1996).
Adams, "The Potential of Mycoparasites for Biological Control of Plant Diseases," Annu. Rev. Phytopathol. 28:59–72 (1990).
Agrios, *Plant Pathology*, 2nd ed., Academic Press, New York, p. 122 (1978).
Chivukula et al., "Lignin Peroxidase–Catalyzed Oxidation of Sulfonated Axo Dyes Generates Novel Sulfophenyl Hydroperoxides," Biochemistry 34:7765–7772 (1995).
Chong, "Apple Pomace as an Amendment in Container Growing Media," HortScience 27:1138, (1992).
Field et al., "Biodegradation of Polycyclic Aromatic Hydrocarbons by New Isolates of White Rot Fungi," Appl. & Environment Microbiol. 58:2219–2226 (1992).
Glenn et al., "Decolorization of Several Polymeric Dyes by the Lignin–Degrading Basidiomycete *Phanerochete chrysosporium*," Appl. & Environmental Microbiol. 45:1741–1747 (1983).
Haemmerli et al., "Oxidation of Benzo(a)pyrene by Extracellular Ligninases Of *Phanerochaete Chrysosporium*," J. Biol. Chem. 261:6900–6903 (1986).
Hang, "Production of Fuels and Chemicals from Apple Pomace," Food Technology 41:115–117 (1987).
Hang, "Recovery of Food Ingredients from Grape Pomace," Biochem. Feb. 1988, pp. 2–4 (1988).
Hours et al., "Microbial Biomass Product from Apple Pomace in Batch and Fed Batch Cultures," Appl. Microbiol. Biotechnol. 23:33–37 (1985).
Jewell et al., "Apple Pomace Energy and Solids Recovery", J. Food. Sci. 49:407–410 (1984).
Katayama et al., "Degradation of Organochlorine Pesticides, Particularly Endosulfan, by *Trichoderma Harzianum*," Environmental Toxicology and Lchemistry 12:1059–1065 (1993).
Knudsen et al., "Method to Enhance Growth and Sporulation of Pelletuzed Biocontrol Fungi," Applied & Environmental Microbiology 57:2864–2867 (1991).
LaCotte et al., "In vitro Biodegradation of Arabian Light 250 by a Marine Mixed Culture Using Fertilizers as Nitrogen and Phosphorous Sources," Chemosphere 31:4351–4358 (1995).
Lo et al., "Biological Control of Trfgrass Diseases with a Rhizosphere Competent Strain of *Trichoderma harzianum*," Plant Disease 80:736–741 (1996).
Okeke et al., "Influence of Environmental Parameters in Pentachlorophenol Biotransformation in Soil by *Lentinula edodes* and *Phanerochaete chrysosporium*," Appl. Microbiol. Biotechnol. 45:263–266 (1996).
Patil et al., "Degradation of the Endrin, Aldrin, and DDT by Soil Microorganisms," Appl. Microbiol. 19:879–881 (1970).
South et al., Germinant sowing in South Africa. Combined Proceedings International Plant Propagator's Society 44:266–270 (http://www.forestry.auburn.edu/coops/sfnmc/pubs/manuscri/nurs–mgt/germsow.html) (1994).
Trevors et al., "Survival of Alginate–Encapsulated *Pseudomonas fluorescens* Cells in Soil," Appl. Microbiol Biotechnol. 39:637–643 (1993).
Worrall et al., "Shiitake and Oyster Mushroom Production on Apple Pomace and Sawdust," HortScience 27:1131–1133 (1992).
Zheng et al., "The Future of Biotechnology as We Approach the 21st Centrury," Apple Processing Wastes as Carrier for *Trichoderma* spp. Inoculants for Use in Bioremediation and Plant Patheogen Control, Poster at MIT conference, (1996).

*Primary Examiner*—Jean C. Witz
*Attorney, Agent, or Firm*—Fish & Richardson P.C.

[57] ABSTRACT

The invention is based on the discovery that fruit pomace, the solid waste presscake left behind after fruit processing, can be used as a growth substrate for microorganisms that inhibit plant pathogens or degrade pollutants, or both. A composition can be made from fruit pomace by adding nitrogen, adjusting the pH, inoculating the pomace with a selected microorganism, and allowing the microorganism to grow in the pomace. The pomace composition is then used as a vehicle for suppression of plant pathogens or bioremediation.

19 Claims, 6 Drawing Sheets

FRUIT POMACE COMPOSITIONS AND USES THEREOF

BACKGROUND OF THE INVENTION

The invention relates to new fruit pomace compositions and methods of using these compositions, e.g., for plant pathogen control and bioremediation.

Pomace is the solid waste presscake left behind after fruit processing. It is difficult to dispose of because its high water content prevents it from composting well. Further, pomace also has a low pH, and high carbohydrate and low protein content, limiting its usefulness as an animal feed. Over one million metric tons of apple pomace alone are produced each year in the United States, and disposal fees are estimated to exceed $10 million. The grape industry produces nearly five million tons of grapes each year, over 40% of which is used for processing purposes. Pomace accounts for as much as 20% of the wet weight of the fruit, and annual production of pomace is over 400,000 tons per year.

Fruit pomace has been used as a raw material to produce certain commercial products, such as ethanol, acetic acid, citric acid, and some dyes and colorants. Pomace has also been inoculated with fungi, such as *Trichoderma reesei*, *Saccharomyces lipolytica*, and others, as a means to increase the protein content in the pomace, and increase its value as a cattle feed. Edible mushrooms such as shiitake and oyster mushrooms have also been grown on a pomace substrate, but there is still far more pomace produced than can be used in these ways.

Trichoderma is a fungus known to parasitize a number of other soil-borne fungi that are pathogenic to plants. Much research has been done to determine ways to exploit this natural inhibition of plant pathogens. Few practical applications have resulted, however, mostly because the beneficial fungi are out-competed by other native fungi under typical field conditions.

Many other organisms have been shown to parasitize plant pathogens, including *Pythium nunn*, which attacks *P. ultimum* (damping-off of cucumber), *Rhizoctonia solani* (root rot), and *Phytophthora parasitica* (buckeye rot of tomato). *Talaromyces flavus* is particularly aggressive, and suppresses *R. solani* root rot, *Sclerotinia sclerotiorum* wilt of sunflowers, and Verticillium spp., which causes devastating wilts in a wide variety of crops. Experiments also have been done using *Sporidesmium sclerotivorum* against *Sclerotinia minor*, which causes lettuce drop, but current methods of culturing Sporidesmium have proved uneconomical for field use. Several fungi, including *Teratosperma oligocladum*, *Suillus granulatus*, Peniophora spp., and *Pisolithus tinctorius* are thought to have potential uses in forestry applications, in preventing root rot in pine species from Rhizoctonia spp. and Phytophthora spp.

Bioremediation is the use of organisms to remove pollutants from the environment. Several naturally-occurring microorganisms exist that degrade organic pollutants, such as *Phanerochaete chrysosporium* strain BKM-F-1767, Trametes spp., and *Bjerkandera adusta*. These three fungi are known to degrade polycyclic hydrocarbons, including fluorene and benzo[a] pyrene, and have potential use in bioremediation of contaminated soil. Strains of Pseudomonas spp., Alcaligenes, spp., Acinetobacter spp., and *Marinobacter hydrocarbonoclasticus* have been found growing in petroleum-contaminated marine sediments, and could be used to clean up oil spills. In the field, however, additives must usually be applied to the substrate to promote the growth of these microorganisms. Oleophilic fertilizers are often used, because the nutrients dissolve into the oil and also allow microbial growth at the oil-water boundary (LaCotte, et al., 1995, Chemosphere 31:4351).

SUMMARY OF THE INVENTION

The invention is based on the discovery that fruit pomace can be used as a growth substrate for microorganisms that inhibit plant pathogens or degrade pollutants, or both. Pomace supports the growth of a variety of microorganisms, including Aspergillus spp., Saccharomyces spp. (yeast), *Pleurotus ostreatus* (oyster mushroom), and *Lentinula edodes* (shiitake mushroom). Two fungi which grow well on pomace are Trichoderma, which inhibits fungi pathogenic to plants, and Penicillium, which excretes antibacterial toxins.

In general, the invention features a method of using a fruit pomace composition for controlling plant pathogens. The method includes obtaining a fruit pomace, e.g., one or more of apple, grape, cranberry, orange, or strawberry, adding a nitrogen source e.g., fish protein hydrolysate, unhydrolysed fish waste, fish meal, or fish gurry in an amount adequate to support growth of a microorganism that inhibits a plant pathogen, adjusting the pH of the pomace to achieve a pH adequate to support growth of the microorganism, inoculating the pomace with the microorganism to form a composition, mixing the composition to form a homogeneous mixture and culturing the mixture for a time sufficient to allow the microorganism to grow, and applying the pomace composition to a plant to be protected from the plant pathogen. The microorganisms used can be one or more of Trichoderma spp., Penicillium spp., *Pythium nunn, Talaromyces flavus, Sporidesmium sclerotivorum, Teratosperma oligocladum, Suillus granulatus, Pisolithus tinctorius*, or Peniophora spp. The pomace composition can be applied to the subtrate in which the plant is growing, or to the stem, trunk, or roots of the plant, or to the plant in seed form. The pomace composition can also be applied to seeds or plant propagules by fluid drilling.

In another aspect, the invention features a fruit pomace composition which includes a fruit pomace, a nitrogen source, an acidic or basic compound to adjust the pH, and a microorganism, as described above, which are mixed in proportions to form a homogenous composition having a pH of 4.0 to 6.5 and a nitrogen concentration of 3% to 10%.

The invention also features a method of using a fruit pomace composition for bioremediation of a compound in a substrate. The method includes obtaining a fruit pomace, e.g., apple, grape, cranberry, orange, and strawberry, adding a nitrogen source, e.g., fish protein hydrolysate, unhydrolysed fish waste, fish meal, and fish gurry, to the pomace in an amount adequate to support growth of a microorganism that degrades the compound in the substrate, adjusting pH of the pomace to achieve a pH adequate to support growth of the microorganism, inoculating the pomace with the microorganism to form a composition, mixing the composition to form a homogeneous mixture and culturing the mixture for a time sufficient to allow the microorganism to grow, and applying the pomace composition to the substrate to effect bioremediation of the compound. The microorganisms used can be one or more of Trichoderma spp., *Phanerochaete chrysosporium*, Pseudomonas spp., Alcaligenes spp., Acinetobacter spp., *Marinobacter hydrocarbonoclasticus* and Penicillium spp. The compounds to be removed from the substrate can be aromatic compounds, hydrocarbons, petrochemicals, phenol, hydroquinones, benzoquinones, azo dyes, or organic compounds. The compounds can also be pesticides, such as DDT, dieldrin, endosulfan, pentachloronitrobenzene, or pentachlorophenol. The substrate to be treated with the bioremediation composition can be, for example, a landfill, soil, or liquid such as waste water.

As used herein, the term "bioremediation," means the use of organisms, such as plants or microbes, to selectively remove or degrade undesirable compounds from a substrate.

A "microorganism" is any organism of microscopic size, including single- and multicellular organisms, fungi, bacteria, and algae.

A "plant pathogen" is any organism that parasitizes or lives on a plant and inhibits its growth or yield, or both.

A "plant substrate" is any substrate or support system provided to a plant for the purpose of support. Thus, a plant substrate can be soil, sand, peat moss, vermiculite, or any other naturally-occurring or man-made material used for growing plants, seeds, shoots, cuttings, or propagules.

As used herein, "fluid drilling," means a method of mechanical sowing where plant seed or propagules are mixed with a fluid or viscous, gel-like substance, and a hollow needle attached to a vacuum apparatus is used to isolate one or more seeds from the fluid reservoir, push them into the soil, and release the seeds with a simultaneous injection into the soil of the reservoir fluid.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents and other references mentioned herein are incorporated by reference in their entirety. In case of conflict, the present specification, including definitions, will control. In addition, the materials, methods, and examples are illustrative only and not intended to be limiting.

An advantage of the invention is that it provides a variety of new uses for an industrial waste product which is currently difficult to dispose of economically and effectively.

An additional advantage of the invention is that the fruit pomace acclimates the added microorganisms to a solid substrate.

Other features and advantages of the invention will be apparent from the following detailed description, and from the claims.

DETAILED DESCRIPTION

Figure 1:
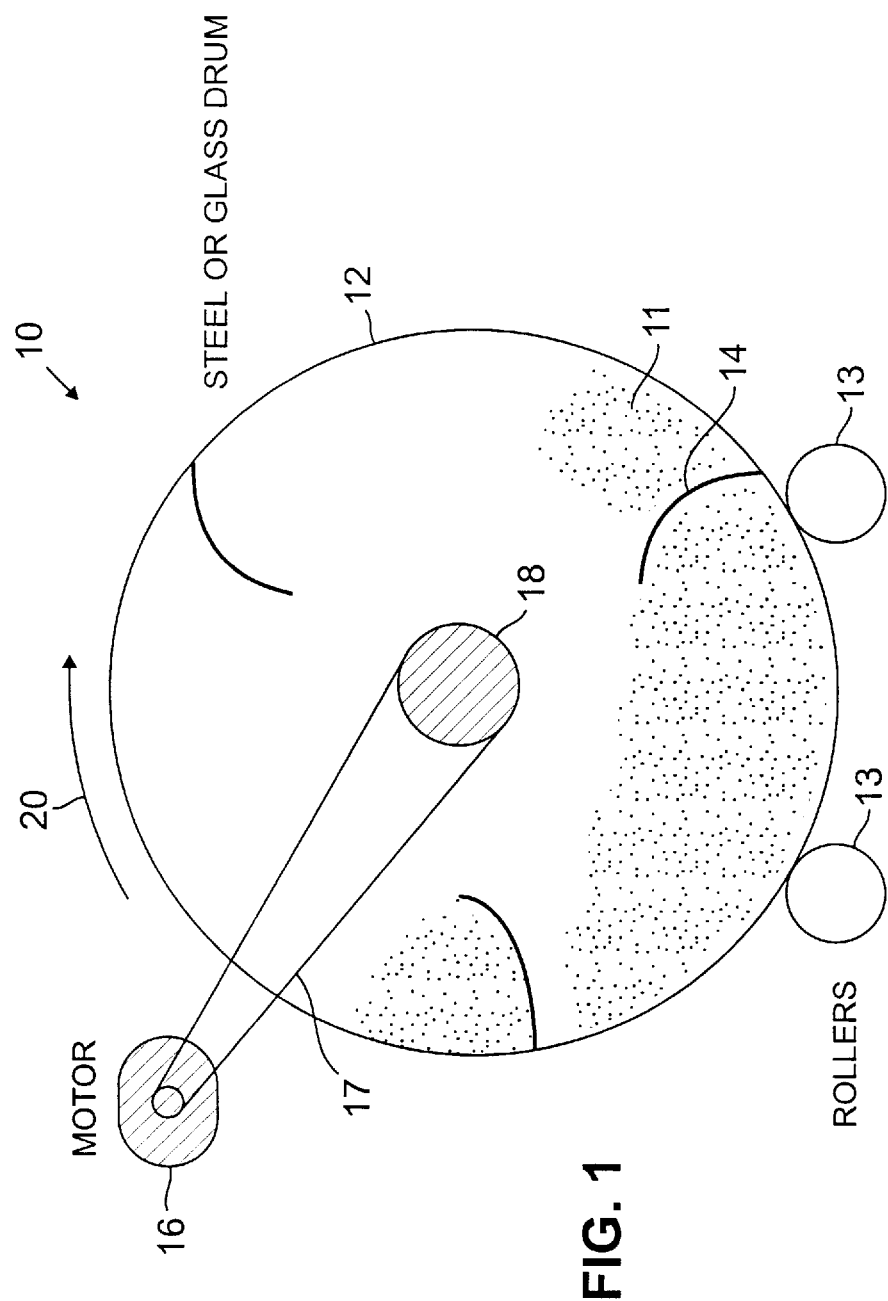
FIG. 1 is a schematic in partial cross-section, illustrating a ten-liter rotating drum bioreactor for large-scale production of the pomace mixture.

Fruit pomace, the solid waste left behind after fruit processing, normally constitutes a waste disposal problem due to its high water content, chemical composition, and sheer volume. The invention is based on the discovery that pomace can serve as a substrate for the growth of useful microorganisms. The fungus Trichoderma, for instance, which parasitizes some plant pathogens, grows well in apple pomace, and is also known to be lignolytic. The lignin degradation system is mediated by lignin peroxidase, which initiates azo dye degradation (Chivukula, et al., 1995, Biochemistry 34:7765) and oxidation of polycyclic aromatic hydrocarbons in vitro (Haemmerli, et al. 1986, J. Biol. Chem. 261:6900). Trichoderma therefore has dual use in controlling plant pathogens and also in bioremediation. Other microorganisms which parasitize plant pathogens and/or metabolize and degrade organic pollutants, also grow well on fruit pomace. Growth of any of these organisms in pomace creates a naturally-derived composition which can be tilled into the soil to either protect crops, or to degrade harmful pollutants and toxins, and thus provides an efficient and economical use of the pomace, which would otherwise cause a disposal problem. In addition, fish hydrolysate, another waste product, can be added to the pomace substrate to increase its nutrient value, enhancing growth of both the plants being protected, and the beneficial microorganisms themselves.

Preparation of Pomace Compositions

Apple and other fruit pomaces contain a high concentration of carbohydrates, but have a low pH (3.1 to 3.8) and low nitrogen concentration. For good growth of microorganisms, the pH should be increased to a range of 4.5 to 5.5, and a nitrogen source must be added to provide a nitrogen concentration of 3 to 8% by dry weight. The nitrogen source can be, for example, ammonium nitrate, fish protein hydrolysate, yeast extract, or bactopeptone. Additional water is also required, because fresh pomace consists mostly of solids.

A suitable medium for microbial growth consists of (by weight) 10 parts dry pomace, 25 parts water, and 0.5 parts each of calcium carbonate ($CaCO_3$) and ammonium nitrate ($NH_4NO_3$). The water content of dried apple pomace is about 10%, and water should be added to give a final concentration of about 30% to 40% water. Fresh apple pomace contains about 80% water, and should be pressed or dried to reduce the moisture level to about 30 to 40%. Fish protein hydrolysate can be substituted for ammonium nitrate, and may be a cost-effective alternative in large-scale production. In the composition described above, 3 parts of herring waste containing 0.6575 grams per milliliter of protein can be substituted for the ammonium nitrate, yielding about 320 milligrams of total nitrogen, or about 3%, although the total nitrogen content can be brought as high as 8%. Fish protein hydrolysate is produced by acid hydrolysis with phosphoric acid, and has a pH of about 4.0. Most fruits are also acidic, so pH adjustment of the pomace composition should be done, e.g., with calcium carbonate after the fish protein hydrolysate has been added, to bring the pH into a range of about 4.0 to 6.5. Should it ever be necessary to lower the pH, this can be done with potassium hydroxide, or other bases.

This formulation was found to work with a variety of different fruit pomaces. For pomace from unusual fruits such as tropical fruits, the variables of water content, pH, and nitrogen content can be easily optimized by adding enough water to bring the water content to about 30% to 40%, $CaCO_3$ in sufficient quantity to adjust the pH to the range of 4.0 to 6.5, and fish waste to provide 3 to 8% total nitrogen.

The composition described above is easily made in large batches. FIG. 1 shows a rotating-drum bioreactor 10 including a drum 12, made of steel or glass, containing pomace composition 11. The drum 12 rests on its side on two rollers 13, and is driven by motor 16 via a belt or chain 17, rotating on central axis 18 in the direction of rotation shown by arrow 20. The inner wall of drum 12 includes three curved mixing vanes 14 running lengthwise on the inside of the drum. The vanes are slightly cupped so that as the drum rotates, a portion of the pomace mixture 11 is carried upward, and is dropped when the vane approaches its uppermost position. The drum 12 holds a specific amount, e.g., ten liters, of the pomace composition. The drum is rotated slowly (e.g., 2–5 revolutions per minute) and provides mixing of composition ingredients, distribution of microbial inoculum, sufficient aeration for microbial growth and colonization, and adequate mixing to provide a homogeneous composition. The simple design of the bioreactor allows it to be scaled up for larger batches and it can be constructed of easily obtained materials.

Under the conditions described above, maximum growth of a given microorganism is generally achieved in five to seven days. Scale-up to the bioreactor is done stepwise with inoculation from an agar slant of purified strains, into 100 milliliter flask culture for 4 days. These small cultures are then used to inoculate larger 2 to 4 liter cultures, which after 4 to 5 days are used to inoculate the large bioreactor described above. A bioreactor full of inoculum can be made from an agar slant in two to three weeks.

The pomace composition described above is intended to be used immediately. A dry, pelletized form of the pomace composition allows easier distribution and storage. To formulate a pelleted form of the pomace composition, the pomace should be inoculated with microorganisms as described above, and allowed to grow for five days. Trichoderma begins sporulating after only three days' growth on the pomace medium, although it is recommended to allow five days' growth to attain the highest spore concentration feasible. The optimum working density is $10^{12}$ colony forming units (conidia) per milliliter. The pomace composition can be centrifuged to increase the concentration of conidia if necessary, or diluted with sterile demineralized water or sterile filtered uninoculated pomace to dilute the concentration of conidia. The composition containing the sporulated microorganisms are then encapsulated, for example, as follows.

Sodium alginate (Fluka, Ronkonkoma, N.Y., USA) solution in demineralized water is prepared at a concentration of 2% (weight/volume) and autoclaved at 121° C. for 10 minutes. Equal parts of the sodium alginate solution and the pomace composition are mixed to achieve a final concentration of 1% sodium alginate, and $10^6$ conidia per milliliter. The mixture is then extruded dropwise out of a sterile needle into 0.1 molar $CaCl_2$ (aqueous solution) to form beads. The resulting pellets are removed by screening, and are dried at 22° C. to 25° C.

The pellets can be stored, transported, or used as is, but hyphal growth of inoculated fungi is significantly increased by a subsequent treatment of the dried pellets by soaking in 40% polyethylene glycol (aqueous solution) for 16 hours at 22° C., followed by an additional air drying. This pelletized form can be hydrated, the microorganisms allowed to grow for several days, and the pomace composition would then be used in various applications, e.g., as described below.

Plant Pathogen Inhibition

For nursery and horticultural applications the pomace composition is added directly to potting mix. Optimal ratios of volume of pomace composition to volume of potting mix are evaluated for the species of plant grown, but generally, the pomace composition can be substituted for up to 75% of the potting mix for short-term applications, such as flats of seedlings which are used by home gardeners, and are soon transplanted directly into the ground. For plants that are kept in a single container for a longer period of time, such as office plants or woody shrubs and young trees, the pomace composition should not make up more than 50% of the volume of the container, because shrinkage of the pomace over time can reach rates greater than 20% of the total container volume over two years.

For agricultural applications, the pomace composition can be spread directly onto a field and tilled into the soil as is currently done with compost or chemical fertilizer. Amounts of about 100 to 200 kilograms per hectare, disked into the upper 6 to 8 inches of soil, should be sufficient for general protection of crops from soil-borne pathogens. For areas suffering from unusually heavy pathogenic infestations, more pomace composition can be tilled into the soil as needed. Unlike chemical fertilizers or fungicides, fruit pomace will neither "burn" existing plants nor contaminate ground water.

There many fungi and microbes that have been found that inhibit plant pathogens, but their potential use has been limited by the inability to economically culture a sufficient inoculum to be effective in the field. Fruit pomace is a waste product, and is cheaper than microbiological media. The microorganisms can be grown in the fruit pomace composition, and used to suppress a wide variety of soil-borne plant pathogens. To work out optimum treatment conditions in these situations, test plants are grown in infected or sterilized soil, both of which are treated with varying amounts of the pomace composition. Germination, seedling emergence, general plant survival and growth, and harvested dry weight are measured to determine the lowest level of treatment necessary to inhibit the pathogen. If the objective is to "cut" the pomace-microbe mixture, it is important to dilute the inoculated pomace with fresh pomace when conducting experiments. The uninoculated pomace itself has a fertilizer effect. Reducing the amount used in an experiment may reduce plant performance by lowering this effect, rather than by lowering the amount of pathogen protection, thereby suggesting that one should use a larger volume of pomace composition in the field than that actually required.

Fruit pomace is a useful culture and delivery vehicle for many microorganisms that inhibit plant pathogens. Examples include *Pythium nunn*, which attacks *P. ultimum* (damping-off of cucumber), *Rhizoctonia solani* (root rot), and *Phytophthora parasitica* (buckeye rot of tomato); *Talaromyces flavus*, which suppresses *R. solani* root rot, *Sclerotinium sclerotiorum* wilt of sunflowers, and Verticillium spp, which causes devastating wilts in a wide variety of crops; and *Teratosperma oligocladum* and *Sporidesmium sclerotivorum*, which are highly effective against *Sclerotinia minor* (lettuce drop) (Adams, 1990, Annu. Rev. Phytopathol. 28:59). Other microorganisms such as *Peniophora gigantea*

(Agrios, 1978, Plant Pathology, 2nd ed., Academic Press, New York, p. 122), *Suillus granulatus*, and *Pisolithus tinctorius* (Marx, 1972, Annu. Rev. Phytopathol. 10:429) are thought to have potential uses in forestry applications in preventing root rot in pine species from Rhizoctonia spp. and Phytophthora spp.

Many plants are stored or shipped with bare roots or with only minimal soil around the roots. This is the way most home gardeners receive fruit trees, shrubs, and thick-rooted perennials by mail. Dipping the roots into the pomace composition as the plants are harvested, or packing them in a "ball" of the pomace for shipping, ensures protection against soil-borne pathogens when planted by the home gardener.

In addition, the pomace composition, when applied to freshly pruned branches and new grafts on trees and shrubs, will protect the wounds against entry by pathogenic organisms. Because the pomace composition relies on the activity of a living organism, however, it cannot be heated and compounded with resins or waxes. Therefore, to prevent the pomace from being removed by weather, the area to which the composition is applied should be wrapped with cloth or plastic.

The pomace compositions can also be used in fluid drilling, which is a method of mechanical sowing of seed. Seeds are mixed with a gelatinous fluid and placed in a reservoir. A needle attached to a vacuum head is dipped into the reservoir, vacuum is applied, and when the needle is removed, a seed is held onto the needle by the force of the vacuum. The needle is then pushed ("drilled") into the soil, and a predetermined amount of fluid is ejected, releasing the seed into the soil. Choice of needle size and vacuum setting vary according to the size and species of seeds used, but conditions have been worked out for many species of plants, and guidelines are generally provided by the equipment manufacturers. Small hand-operated models for nursery applications and larger models for field use are currently manufactured.

Hydrophilic gels are often used with fluid drilling. These are compounds that hold many times their weight in water, and release it as the local environment becomes dry. There are two types that are commonly used. One contains starch and is rapidly decomposed by bacteria and fungi; the other type is synthetic. The composition of the synthetic hydrogels varies, but they are frequently cross-linked polymers. Unfortunately, the behavior of these compounds in the soil is not well understood, and there have been reports that commonly-occurring soil salts or fertilizer can reduce the polymers' water-absorbing capacity by up to 90%. They are also expensive, and cost about $5.00 to $7.00 per pound or more. The pomace composition can be used in fluid drilling equipment in place of the hydrophilic gels. The pomace composition binds and holds water well because it contains up to 10% fiber and has a high pectin content (1.5 to 2.5%). Pomace also does not have any adverse interactions with water salts or fertilizers.

Bioremediation

Bioremediation is the removal of toxins or contaminants from soil, air, or water by plants or microorganisms. Some plants are known to remove formaldehyde, benzene, or trichloroethylene from the air. Others selectively take up heavy metals from the soil, and have been studied for their use in cleaning contaminated sites at mining operations.

Certain microorganisms also have this capability. For example, Pseudomonas spp. and Bacillus spp. can degrade organochlorine pesticides such as DDT, dieldrin, and endrin (Patil, et al., 1970, Appl. Microbiol. 19:879), and *Trichoderma harzianum* is known to DDT, dieldrin, endosulfan, and also pentachloronitrobenzene, and pentachlorophenol (Katayama & Matsumura, 1993, Environmental Toxicology and Chemistry 12:1059). It also produces peroxidases, two families of which have been shown to initiate azo dye degradation (Chivukula, et al., 1995, Biochemistry 34:7765) and oxidation of polycyclic aromatic hydrocarbons in vitro (Haemmerli, et al. 1986, J. Biol. Chem. 261:6900). *Phanerochaete chrysosporium* is well documented for degrading phenolic compounds, hydroquinones, benzoquinones, PCBs, dioxins, benzene, and pentachlorophenol (Yadav & Reddy, 1993, Applied & Environmental Microbiol. 59:2904, Okeke, et al. 1996, Appl. Microbiol. Biotechnol. 45:263).

Other microorganisms are also known to degrade organic pollutants. For instance, strains of Pseudomonas spp., Alcaligenes, spp., Acinetobacter spp., and *Marinobacter hydrocarbonoclasticus* have been found growing in oil-contaminated marine sediment, and have been shown to degrade crude oil (LaCotte, et al., 1995, Chemosphere 31:4351).

Example 3 below shows that Trichoderma reaches peak peroxidase production just after it reaches peak growth, that is, after six to eight days of culture. Concentration of both protein production, used here as an indicator of Trichoderma growth, and peroxidase production were negligible for the first two days after inoculation. The rates of both increased dramatically on the third day, with protein concentrations over 0.2 milligrams per gram of pomace and peroxidase activity at 0.1 units per gram of pomace. Rates continued to increase through day 5 (protein 0.3 milligrams per gram pomace, peroxidase 0.3 units per gram pomace). Protein began to drop, eventually reaching 0.28 milligrams per gram at day 8, while peroxidase reached it peak at day 8 (over 0.4 units per gram pomace) but dropped sharply thereafter.

For bioremediation, Trichoderma should be allowed to grow in the pomace for one to three days longer than when it is used for plant pathogen control. The pomace composition should be tilled directly into the soil to be treated, although care should be taken not to release toxin-bearing dust from the soil during tilling at extremely hazardous sites. Specific amounts of the composition to be applied vary based on the pollution conditions at each site. Application and monitoring of results must be carried out on a case-by-case basis by professionals trained in toxic waste detection and removal. Fruit pomace is a naturally-occurring material, however, and treatment can be repeated as many times as needed with no further harm to the environment. For treatment of beaches, the pomace composition should be tilled into the sand, or spread on the surface if the beach is rocky or if the pollutants have not penetrated the beach surface.

EXAMPLES

Example 1

Large-scale Production of fruit pomace mixture 125-milliliter flasks containing 10 grams of fruit pomace, 25 milliliters of water, 0.5 grams of $CaCO_3$, and either 0.5 grams of $NH_4NO_3$ or 3 milliliters of fish waste (representing about 2 grams of total protein) were inoculated with spores from Trichoderma which was stored on potato dextrose agar. After five days of incubation at room temperature without agitation, the cultures were then used to inoculate 2-liter batches of the same culture medium. After another five days of incubation, the 2-liter cultures were used to inoculate ten liters of the pomace medium in a bioreactor (FIG. 1).

The bioreactor drum is rotated slowly (2–5 revolutions per minute), and provides sufficient aeration for microbial growth and colonization.

Example 2
Comparison of pomace from different fruits

To compare the growth of Trichoderma on pomace from different fruits, the increase in soluble protein produced by *Trichoderma viride* strain IF-26 was measured over several days' culture time. The growth medium consisted of 10 grams of either apple, cranberry, or strawberry pomace, to which was added 25 milliliters of water, 0.5 grams of $CaCO_3$, and 0.5 grams of $NH_4NO_3$. Batches of this medium were placed in 125-milliliter Earlenmeyer flasks, which were inoculated with spores of *Trichoderma viride* strain IF-26, which was stored on potato dextrose agar slants. The cultures were incubated at room temperature for eight days, and soluble protein was measured at twenty-four hour intervals. The levels of soluble protein in the samples were determined using a commercially-available assay kit (Bio-Rad Protein Assay Kit II, Bio-Rad Laboratory, USA) with bovine serum albumin as the standard, according to the manufacturer's instructions. The results are illustrated in FIG. 2.

Figure 2:
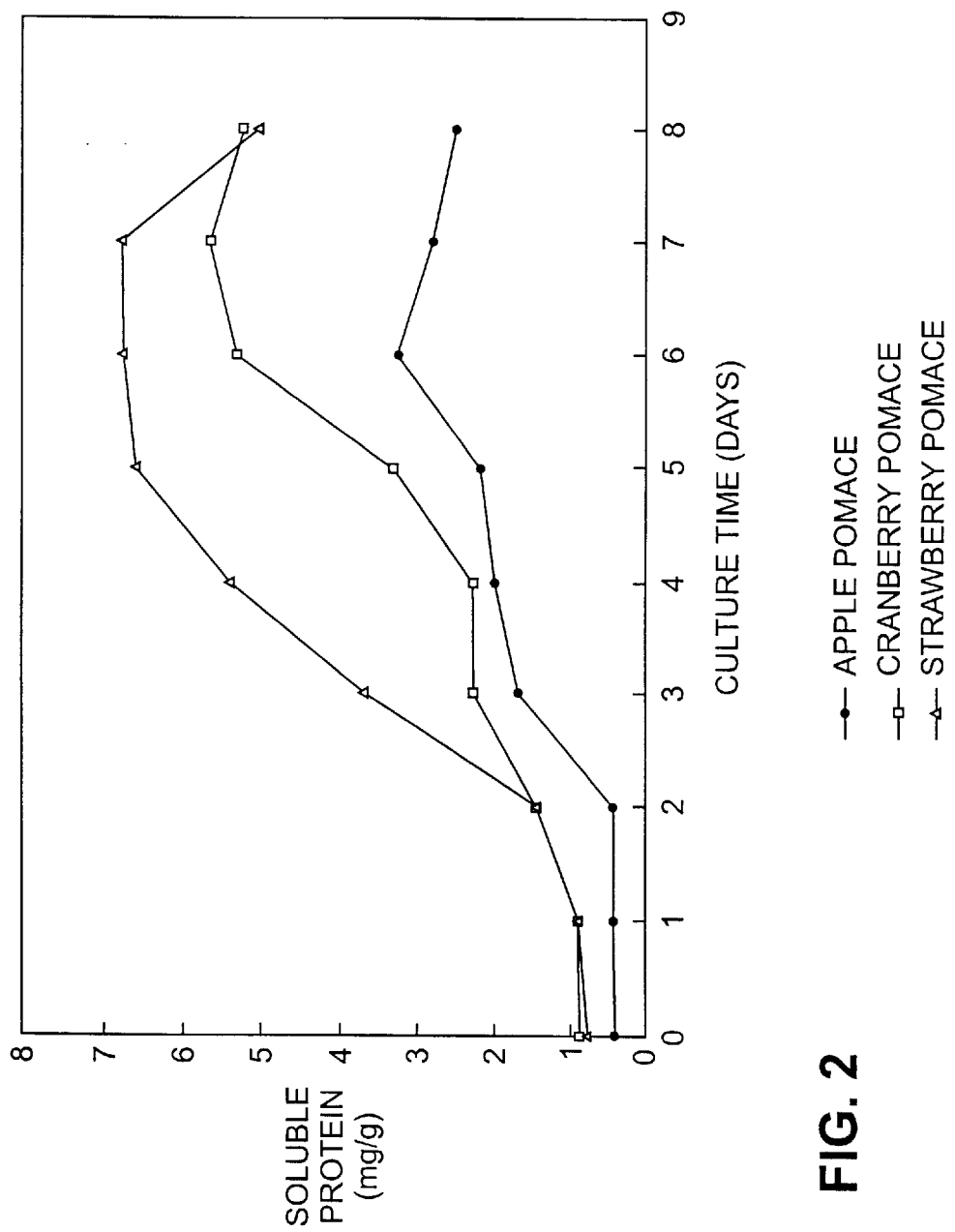
FIG. 2 is a graph illustrating the amount of soluble protein produced by Trichoderma viride strain IF-26 grown on apple (●), cranberry (□), or strawberry (Δ) pomace over eight days of incubation at room temperature.

As shown in the graph of FIG. 2, lag time after inoculation was about two days, with the apple pomace (■) showing no increase in soluble protein, and strawberry (Δ) and cranberry (□) exhibiting a slight increase from 2.0 to 2.5 milligrams protein per gram pomace. The protein content of the apple pomace then increased steadily over the next four days, reaching a peak on day 6 with over three milligrams of soluble protein produced per gram of pomace. Protein production then decreased slightly, dropping to 2.5 milligrams per gram on day 8. Protein production in cranberry pomace increased steadily from day 2 through day 5, from 1.5 milligrams per gram pomace on day 2 to 3.25 milligrams per gram on day 5, and then increased sharply to 5.5 milligrams on day 6. Soluble protein reached a peak of not quite 6 milligrams on day 7, and then dropped back to 5.5 on day 8. Strawberry pomace exhibited the most dramatic production of soluble protein, going from 1.5 milligrams per gram pomace on day 2 to about 6.6 milligrams per gram on day 5. It remained nearly flat for the next two days, then showed a sharp drop to 5 milligrams per gram pomace on day 8.

These results show that of these three fruit pomaces, strawberry pomace was superior in producing a dense inoculum of Trichoderma, but the fungus is readily capable of colonizing all three varieties of fruit pomace substrates.

Example 3
Peroxidase production by Trichoderma

The amount of peroxidase produced by *Trichoderma harzianum* grown on apple pomace medium was monitored. Spores of Trichoderma, stored on potato dextrose agar, were inoculated into flask cultures containing 10 grams apple pomace, 20 milliliters water, 0.5 grams $CaCO_3$ and 0.5 grams $NH_4NO_3$. Samples were removed at 24-hour intervals, and protein and peroxidase were measured. The soluble protein was determined using a commercially-available assay kit (Bio-Rad Protein Assay Kit II, Bio-Rad Laboratory, USA) with bovine serum albumin as the standard, according to the manufacturer's instructions. Peroxidase activity was measured by taking a 3-milliliter sample, adding 100 millimolar of phosphate buffer (pH 7.0) containing 82 micromolar 4-aminoantipyrene, 1 millimolar 2,4-dichlorophenol (DCP), 1 millimolar $H_2O_2$. 0.1 milliliter of enzyme extract was added to the mixture and the change of absorbance at 510 nanometers in the reaction mixture was measured at room temperature. One unit (u) of the enzyme activity is defined as the amount of enzyme which increases the absorbance of the reaction mixture at 510 nanometers by 0.1 nanometer per minute at room temperature. The activity of peroxidase produced by Trichoderma from apple pomace was expressed as units per gram of dry pomace. The results are illustrated in FIG. 3.

Figure 3:
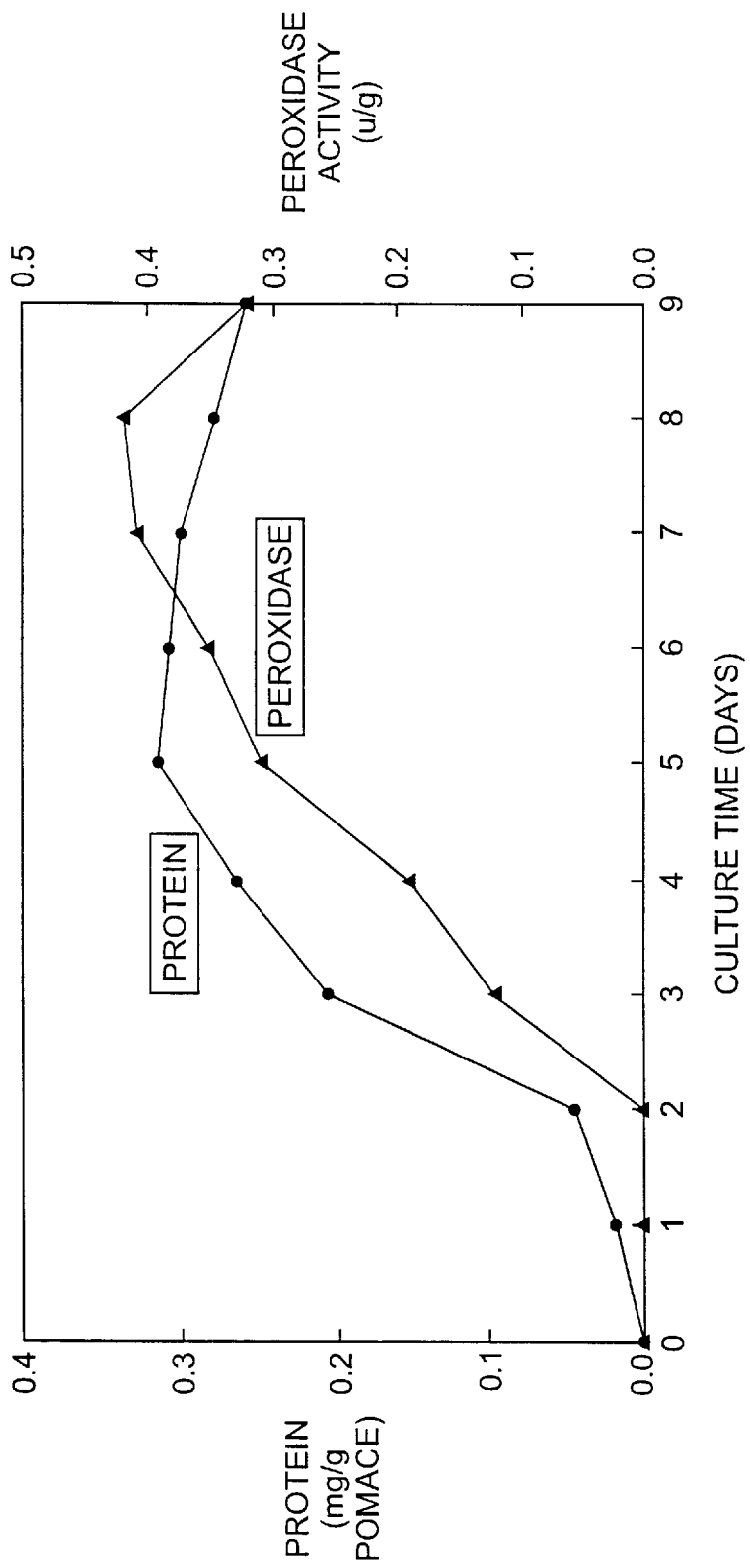
FIG. 3 is a graph illustrating the production of soluble protein (●) and peroxidase (▲) by Trichoderma harzianum grown on apple pomace for nine days.

As shown in the graph of FIG. 3, for the first two days, peroxidase production (▲) was flat, and soluble protein production (●) rose to just under 0.5 milligrams per gram of pomace. Both rose sharply after that, with protein increasing to a peak of over 0.3 milligrams per gram pomace on day 5, then dropping off steadily to just over 0.25 milligrams on day 9. Peroxidase activity, however, increased steadily from day 2 to day 8, rising from 0.0 units to over 0.4 units per gram pomace.

These results show that for inhibition of plant pathogens, Trichoderma should be allowed to grow for at least four to five days, while for bioremediation, the pomace composition should be cultured for at least five and up to eight days prior to use.

Example 4
Substitution of fish wastes for ammonium nitrate in apple pomace mixture production Spores from three species of Trichoderma (*T. viride* strain IF-26, *T. harzianum* strain ATCC 24274, and *T. pseudokoningii* ATCC 26801) stored on potato dextrose agar were inoculated into flasks containing apple pomace medium (10 grams apple pomace, 20 milliliters water, 0.5 grams $CaCO_3$) and varying amounts of either ammonium nitrate or fish protein hydrolysate were added as a nitrogen source. Fish protein hydrolysate was obtained in the form of herring waste that had been acid hydrolysed with phosphoric acid. Fresh hydrolysate has a pH of about 4.0, which was adjusted by the addition of calcium carbonate to the pomace composition. After four days of incubation at room temperature the soluble protein and glucosamine content of the cultures was measured. Soluble protein was measured using a commercially available assay kit (Bio-Rad Protein Assay Kit II, Bio-Rad Laboratory, USA) with bovine serum albumin as the standard, according to the manufacturer's instructions.

Fish waste contains a large amount of protein and so the protein content of the cultures will rise with increasing amounts of fish waste. Therefore, glucosamine was used as an indicator of successful Trichoderma growth when fish waste was substituted for ammonium nitrate. To measure glucosamine, 100 milliliters of distilled water was added to the culture flask and the mixture was homogenized using a Waring blender. One milliliter of this sample was hydrolyzed by mixing with 2 milliliters of 98% $H_2SO_4$, incubating for twenty-four hours at 25° C., diluting with 47 milliliters of water and autoclaving at 120° C. for one hour. The resulting hydrolysate was then neutralized with NaOH to pH 7.0 and diluted to 100 milliliters. 0.5 milliliter of the diluted hydrolysate was mixed with 0.5 milliliter of $NaNO_2$ and 0.5 milliliter of 5% $KHSO_4$ in a centrifuge tube, and after 15 minutes of intermittent agitation, was centrifuged at 1500 g for 2 minutes. 0.6 milliliter of this supernatant was mixed with 0.5 milliliter of 12.5% $NH_4SO_3NH_2$ and shaken for 3 minutes. 0.2 milliliter of fresh 0.5% MBTH (3-methyl-2-benzo-thiazolinone-hydrazone, Sigma Chemical Company, St. Louis, Mo., U.S.A.) was added, and the sample boiled for 3 minutes. After cooling to room temperature, 0.2 milliliter of 0.5% $FeCl_3$ was added as a reducing agent to develop the color.

After standing for 30 minutes, the absorbance at 650 nanometers was measured. The glucosamine content was calculated as micrograms per gram of pomace relative to uninoculated controls. The results are illustrated in FIGS. 4 through 6.

Figure 4:
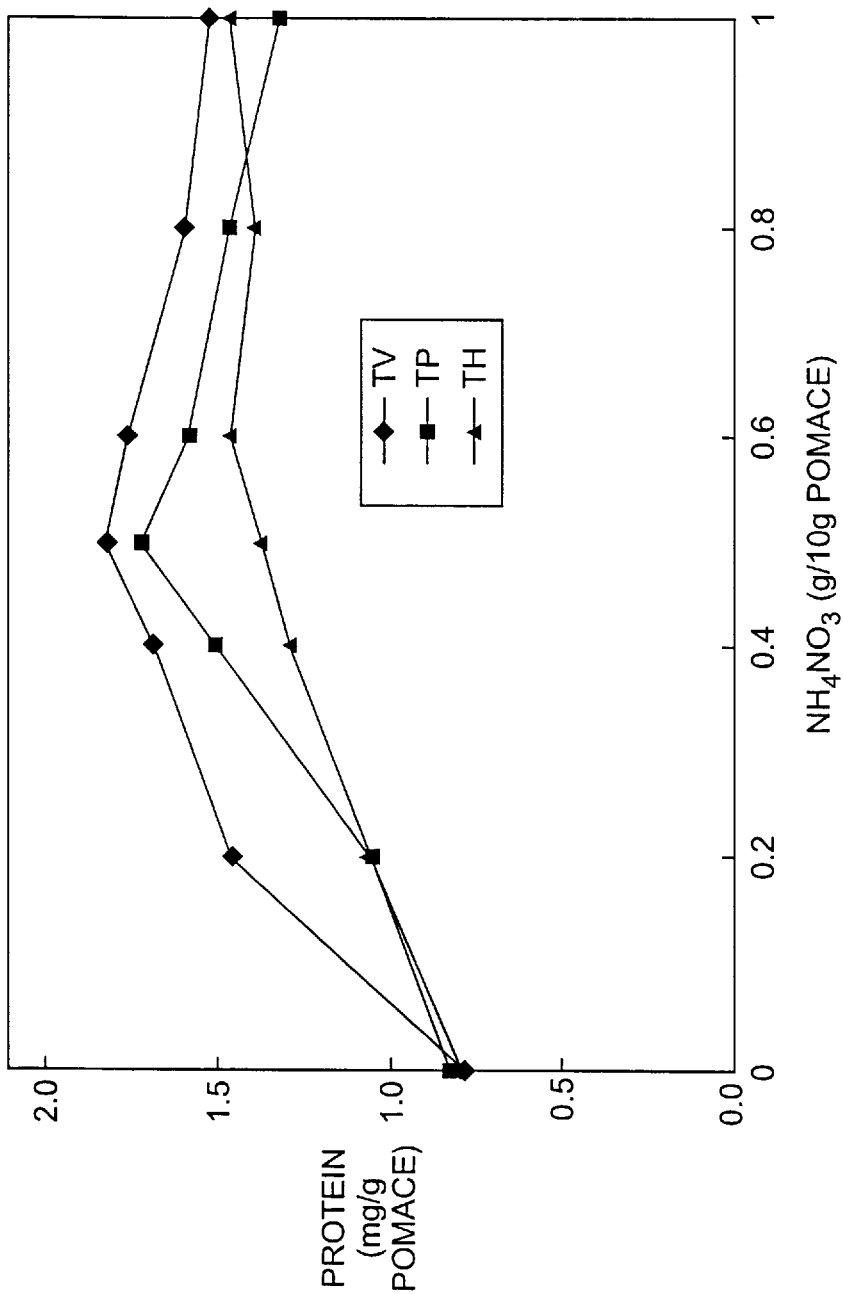
FIG. 4 is a graph illustrating the effect of varying amounts of $NH_4NO_3$ on the growth of three Trichoderma species (T. viride strain IF-26 (♦), T. harzianum strain ATCC 24274 (▲), and T. pseudokoningii ATCC 26801 (■)) in terms of soluble protein production.

FIG. 4 shows the effect of varying amounts of ammonium nitrate on the soluble protein produced. Soluble protein production by Trichoderma viride (♦) and T. pseudokoningii (■) peaked at about 0.5 grams ammonium nitrate per 10 grams pomace in the medium. T. harzianum (▲) peaked at about 0.6 grams $NH_4NO_3$ per 10 grams of pomace and was flat at higher levels.

Figure 5:
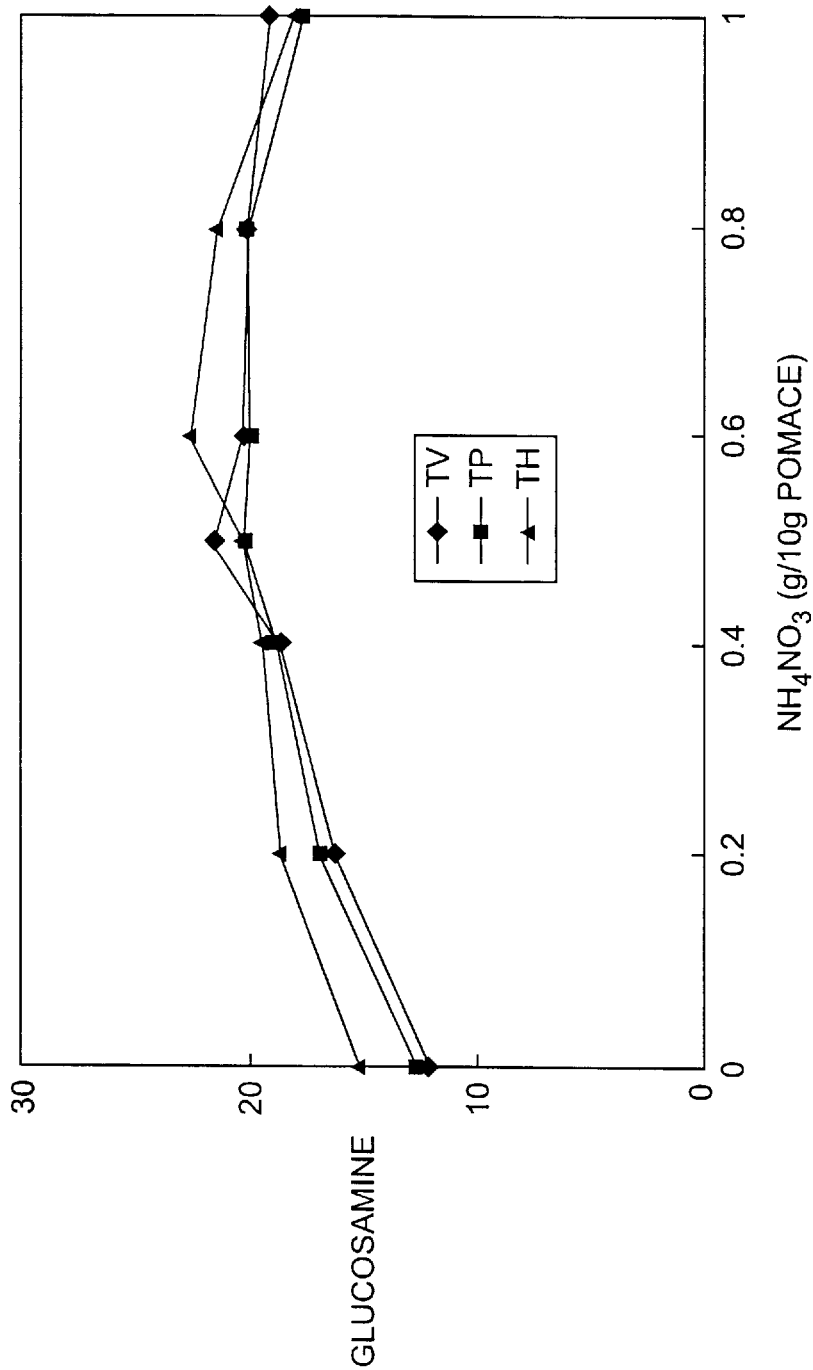
FIG. 5 is a graph illustrating the effect of varying amounts of $NH_4NO_3$ on the growth of three Trichoderma species (T. viride strain IF-26 (♦), T. harzianum strain ATCC 24274 (▲), and T. pseudokoningii ATCC 26801 (E)) in terms of glucosamine production.

FIG. 5 shows the effect of increasing amounts of $NH_4NO_3$ on the glucosamine production by the three Trichoderma species. As expected from the results of FIG. 4, the production of glucosamine for T. viride (♦) and T. pseudokoningii (■) peaked at 0.5 grams per 10 grams of pomace, while T. harzianum (♦) peaked at 0.6 grams.

Figure 6:
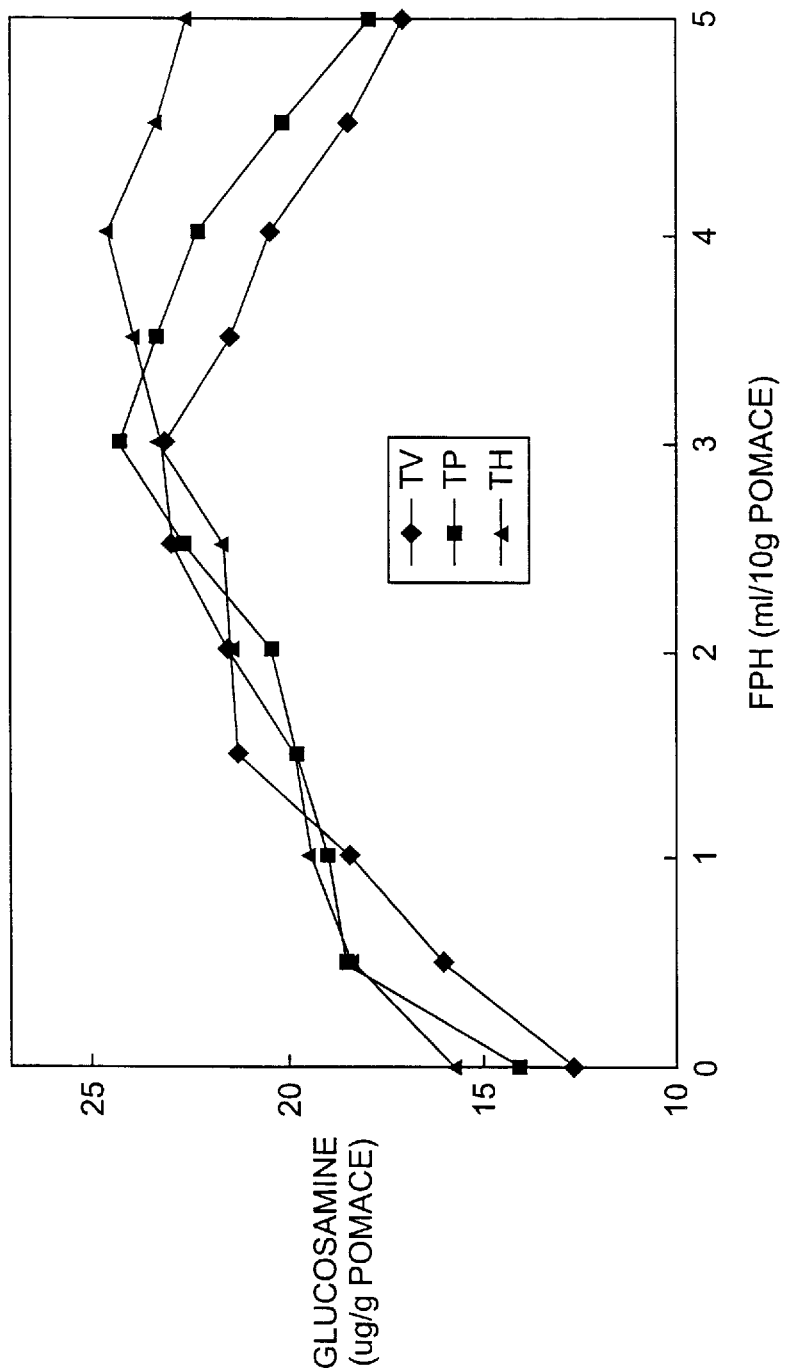
FIG. 6 is a graph illustrating the effect of varying amounts of fish protein hydrolysate (in the form of herring waste) on the growth of three Trichoderma species (T. viride strain IF-26 (♦), T. harzianum strain ATCC 24274 (▲), and T. pseudokoningii ATCC 26801 (■)) in terms of glucosamine production.

FIG. 6 illustrates the effect of increasing amounts of herring waste on glucosamine production by three species of Trichoderma. For T. viride (♦), glucosamine production peaked at levels of 2.5 to 3.0 milliliters of herring waste added per 10 grams of pomace. T. pseudokoningii (■) exhibited peak glucosamine production at 3.0 milliliters per grams of pomace. Peak glucosamine production for T. harzianum (▲) occurred at 4.0 milliliters herring waste added per 10 grams of pomace.

These results demonstrate that fish waste is a suitable substitute for $NH_4NO_3$ as a nitrogen source in production of Trichoderma inoculum on apple pomace.

Example 5
Breakdown of crude oil by Trichoderma spp.

Spores from three species of Trichoderma (T. viride strain IF-26, T. harzianum strain ATCC 24274, and T. pseudokoningii ATCC 26801) stored on potato dextrose agar are inoculated into flasks containing apple pomace medium (10 grams apple pomace, 20 milliliters water, 0.5 grams $CaCO_3$ and 0.5 grams $NH_4NO_3$ is added as a nitrogen source). After eight days of incubation at room temperature, diesel oil is added to a final concentration of 0.01, 0.10, 0.50, 0.75, 1.0, 1.5, and 2.0 grams per liter of pomace medium. The flasks are incubated at room temperature, with agitation. After three days, samples from the flasks are analyzed for the presence of diesel oil.

The samples are acidified with concentrated HCl to pH 2.0, and extracted three times with 25 milliliters $CH_2Cl_2$. The extract is then saponified with methanolic potash (0.5 Normal, 50 milliliters) and toluene (25 milliliters) to extract the organic matter. This organic matter fraction is analyzed via gas chromatography and mass spectrometry to determine the degradation of alkanes and isoprenoids. The drop in alkane and isoprenoid peaks reveals which strains are most aggressive in crude oil breakdown.

Example 6
Degradation of azo dyes by Trichoderma spp.

Spores of Trichoderma harzianum, T. viride, and T. pseudokoningii, stored on potato dextrose agar, are inoculated into flask cultures containing 10 grams apple pomace, 20 milliliters water, 0.5 grams $CaCO_3$, 0.5 grams $NH_4NO_3$. After five days of incubation at room temperature, azo dye Poly R-478, Poly B-411, or Poly Y-606 is added to the cultures to a final concentration of 0.02% (weight/volume). Aliquots are then taken at 1-hour intervals for 12 hours. The aliquots are diluted 10-fold, filtered, and absorbance is measured in a Genesys Spectrophotometer (Spectronic, Inc., Rochester, N.Y.) to determine the rate of decolorization of the dye. Absorbance is measured at $A_{520}/A_{350}$ for Poly R-478, $A_{593}/A_{483}$ for Poly B-411, and $A_{430}/A_{392}$ for Poly Y-606. These paired wavelengths produce the greatest change in the absorbance ratio as each of the dyes is degraded (Glenn & Gold, 1983, Appl. & Environmental Microbiol. 45:1741). The microbial strains most aggressive in azo dye degradation are revealed by comparison of the rate of dye decolorization over time.

Rate of decolorization of Poly R-478 has been correlated with degradation of anthracene and benzo [a] pyrene, which are polycyclic aromatic hydrocarbons (Field et al., 1992, Appl. & Environmental Microbiol. 58:2219). In studying strains of Phanerochaete chrysosporium, Trametes versicolor, and Bjerkandera adusta, Field et al. found that azo dye decolorization and lignin-degrading ability in general were useful indicators of the fungi's ability to degrade polycyclic aromatic hydrocarbons.

Example 7
Effect of nitrogen on dye decolorization

Lignin peroxidase initiates azo dye degradation, and the lignin degradation system has been reported to be repressed in high-nitrogen environments (Glenn & Gold, 1983, Appl. & Environmental Microbiol. 45:1741). To determine the optimal nitrogen concentration for bioremediation, spores from three species of Trichoderma (T. viride strain IF-26, T. harzianum strain ATCC 24274, and T. pseudokoningii ATCC 26801) stored on potato dextrose agar are inoculated into flasks containing apple pomace medium consisting of 10 grams apple pomace, 20 milliliters water, 0.5 grams $CaCO_3$, and either 0, 0.2, 0.4, 0.5, 0.6, 0.8, or 1.0 grams $NH_4NO_3$ added as a nitrogen source. Azo dye Poly R-478 is added to each flask to a final concentration of 0.02% (weight/volume). Aliquots are taken at 1-hour intervals for 12 hours, diluted 10-fold, filtered, and the absorbance at $A_{520}/A_{350}$ measured in a Genesys Spectrophotometer (Spectronic, Inc., Rochester, N.Y.) to determine the rate of decolorization of the dye. The experiment is performed in triplicate, and the optimal nitrogen concentration for azo dye degradation is determined by comparison of the speed of dye decolorization for each of the nitrogen concentrations.

For use in bioremediation, the microorganisms are grown with the nitrogen levels of 3 to 8% as described above in Examples 3 and 4. After a period of eight days of growth on the pomace medium, the nitrogen level is adjusted to the level that was determined as optimal for azo dye decolorization, as described in this Example. Adjustment can be made by addition of more nitrogen, or dilution with additional fresh pomace. To treat contaminated soil, the nitrogen-adjusted pomace composition is incorporated directly into contaminated soil. To treat contaminated liquids such as water, the composition can be or mixed with sterile soil, vermiculite, or some other suitable solid carrier, and packed into a porous container. Contaminated liquids, e.g., waste water, can then be leached through these porous containers so that hydrocarbons or other pollutants can be degraded and removed.

Other Embodiments

It is to be understood that while the invention has been described in conjunction with the detailed description thereof, that the foregoing description is intended to illustrate and not limit the scope of the invention, which is defined by the scope of the appended claims.

What is claimed is:

1. A method of controlling plant pathogens, the method comprising (a) obtaining a fruit pomace, (b) adding a fish waste by-product as a nitrogen source to the pomace in an amount effective to support growth of a microorganism that inhibits a plant pathogen, (c) adjusting the pH of the pomace to achieve a pH adequate to support growth of the microorganism, wherein said pH is between 4.5 and 6.5, (d) inoculating the pomace with the microorganism to form a composition, (e) mixing the composition to form a homogeneous mixture and culturing the mixture for a time sufficient to allow the microorganism to grow, and (f) applying the pomace composition to a plant in an amount sufficient to protect the plant from the plant pathogen.

2. A method of claim 1, wherein the pomace is selected from the group consisting of apple, grape, cranberry, orange, and strawberry.

3. A method of claim 1, wherein the pomace is apple pomace.

4. A method of claim 1, wherein the fish waste by-product is selected from the group consisting of fish protein hydrolysate, unhydrolysed fish waste, fish meal, and fish gurry.

5. A method of claim 1, wherein the pomace is inoculated with one or more microorganisms selected from the group consisting of Trichoderma spp., Penicillium spp., *Pythium nunn, Talaromyces flavus, Sporidesmium sclerotivorum, Teratosperma oligocladum, Suillus granulatus, Pisolithus tinctorius*, and Peniophora spp.

6. A method of claim 1, wherein the pomace composition is applied to the plant by mixing the composition with a plant substrate in which the plant is growing.

7. A method of claim 1, wherein the composition is applied to the stem or trunk of the plant which is to be protected.

8. A method of claim 1, wherein the composition is applied to the plant in seed form.

9. A method of claim 1, wherein the composition is applied to plants in seed form by fluid drilling.

10. A method of claim 1, wherein the composition is applied to roots of the plant.

11. A method of claim 8, wherein the composition is applied to roots of bareroot plants.

12. A composition for controlling plant pathogens produced by the method comprising:

(a) obtaining a fruit pomace, (b) adding a fish wast by-product as a nitrogen source to the pomace in an amount effective to support growth of a microorganism that inhibits a plant pathogen, (c) adjusting the pH of the pomace to achieve a pH adequate to support growth of the microorganism, wherein said pH is between 4.5 and 6.5, (d) inoculating the pomace with the microorganism to form a composition, (e) mixing the composition for form a homogeneous mixture and culturing the mixture for a time sufficient to allow the microorganism to grow.

13. A composition of claim 12, wherein the pomace is selected from the group consisting of apple, grape, cranberry, orange, and strawberry.

14. A composition of claim 12, wherein the pomace is apple pomace.

15. A composition of claim 12, wherein the fish waste by-product is selected from the group consisting of fish protein hydrolysate, unhydrolysed fish waste, fish meal, and fish gurry.

16. A composition of claim 12, wherein the pomace is inoculated with one or more microorganisms selected from the group consisting of Trichoderma spp., Penicillium spp., *Pythium nunn, Talaromyces flavus, Sporidesmium sclerotivorum, Teratosperma oligocladum, Suillus granulatus, Pisolithus tinctorius*, and Peniophora spp.

17. A composition of claim 15, wherein the pomace is inoculated with one or more microorganisms selected from the group consisting of Trichoderma spp., Penicillium spp., *Pythium nunn, Talaromyces flavus, Sporidesmium sclerotivorum, Teratosperma oligocladum, Suillus granulatus, Pisolithus tinctorius*, and Peniophora spp.

18. The method of claim 1, wherein said pomace has a pH of 5.5 to 6.5.

19. The composition of claim 12, wherein said homogenous composition has a pH from 5.5 to 6.5.

* * * * *